(12) United States Patent
Jett et al.

(10) Patent No.: US 6,623,611 B1
(45) Date of Patent: Sep. 23, 2003

(54) ZIRCALLOY TIPPED ECP SENSOR ELECTRODE

(75) Inventors: Robert Jett, Twinsburg, OH (US); Lucas Clarke, North Canton, OH (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 10/299,839

(22) Filed: Nov. 20, 2002

(51) Int. Cl.[7] .................. G01N 17/02; G01N 27/26
(52) U.S. Cl. ........................... 204/404; 204/293
(58) Field of Search ................. 204/404, 293; 205/775.5–777

(56) References Cited

U.S. PATENT DOCUMENTS

| 4,425,193 | A | * | 1/1984 | Taylor |
| 5,043,053 | A | | 8/1991 | Indig et al. |
| 5,192,414 | A | | 3/1993 | Indig et al. |
| 5,516,413 | A | * | 5/1996 | Foster et al. |
| 6,099,718 | A | * | 8/2000 | Duthoo et al. |
| 6,222,307 | B1 | | 4/2001 | Roy et al. |
| 6,357,284 | B1 | | 3/2002 | Kim et al. |

\* cited by examiner

*Primary Examiner*—T. Tung
(74) *Attorney, Agent, or Firm*—Nixon & Vanderhye P.C.

(57) ABSTRACT

An electrochemical corrosion potential sensor electrode is formed with a zircalloy electrode tip having a closed end and an open end, the open end secured to a ceramic insulator, with a conductor wire extending through the insulator into the electrode tip.

16 Claims, 1 Drawing Sheet

ZIRCALLOY TIPPED ECP SENSOR ELECTRODE

BACKGROUND OF THE INVENTION

This invention relates to electrodes and, more specifically, to a zircalloy tipped electrode for an electrochemical corrosion potential (ECP) sensor.

Existing ECP sensors consist of a platinum tipped sensor, a zirconia ceramic tipped sensor or a stainless steel tipped sensor. The platinum type sensor is used as a standard hydrogen type electrode. This serves as the reference electrode since it has a typical Nernstian response to the hydrogen concentrations in the reactor water. A platinum tipped ECP electrode is disclosed in commonly owned U.S. Pat. No. 6,222,307. Another commonly. owned patent, U.S. Pat. No. 5,192,414, discloses stainless steel or platinum tipped ECP electrodes.

The zirconia ceramic type sensor is a ceramic ECP electrode that contains a metal-metal oxide mixture inside the permeable zirconia ceramic tip. See, for example, commonly owned U.S. Pat. Nos. 5,043,053 and 6,357,284. This type of electrode responds to the oxygen concentrations in the reactor water. The measurement obtained with the zirconia ECP sensors is a raw voltage representing the oxygen concentration and electrical potential of the reactor water. These measurements must be processed through a data acquisition system so that calculations can be performed to obtain concentrations "corrected" to the standard hydrogen electrode scale, which can then be correlated to the corrosion potential of specific surfaces exposed to the reactor water.

The stainless steel electrode is used as a comparative measurement device. The potential measured by this electrode is compared to that of the platinum standard and zirconia ceramic reference electrodes, thus allowing the ECP of the stainless steel surface in a given water chemistry to be directly measured. It would be advantageous to have a similar electrode designed to incorporate a metal tip made of zircalloy instead of stainless steel. This would allow the ECP of zircalloy to be directly measured as compared to the potentials measured by the standard hydrogen and reference zirconia electrodes.

BRIEF DESCRIPTION OF THE INVENTION

The ECP electrode in accordance with the invention includes a metal electrode tip that is closed at one end. The electrode tip is manufactured from zircalloy metal and is used in calculating the electrochemical corrosion potential of zircalloy metal exposed to reactor water through comparison to a standard reference platinum electrode. The zircalloy metal electrode tip is brazed to a ceramic insulator which is, in turn, brazed to an iron-nickel alloy adapter sleeve having a coefficient of thermal expansion which closely matches that of the ceramic insulator. The adapter sleeve is welded to a metal adapter housing, which is in turn secured to a metal coaxial cable. The coaxial cable carries. the electrical signal from the electrode tip to a data acquisition system.

Accordingly, the present invention relates to an ECP sensor electrode comprising an electrode tip, having a closed end and an open end, the open end secured to a ceramic insulator, with a conductor wire extending through the insulator into the electrode tip, and wherein the electrode tip is constructed of zircalloy.

In another aspect, the invention relates to an ECP sensor electrode comprising a zircalloy electrode tip having a closed end and an open end, the open end secured to a ceramic insulator, and a conductor wire extending through the insulator into the electrode tip; wherein the open end is brazed to one end of the ceramic insulator; and an opposite end of the ceramic insulator is brazed to one end of a substantially cylindrical metal adapter sleeve; wherein an opposite end of the metal adapter sleeve is secured to an adapter housing supporting a coaxial cable connected to the conductor wire.

DETAILED DESCRIPTION OF THE INVENTION

Figure 1:
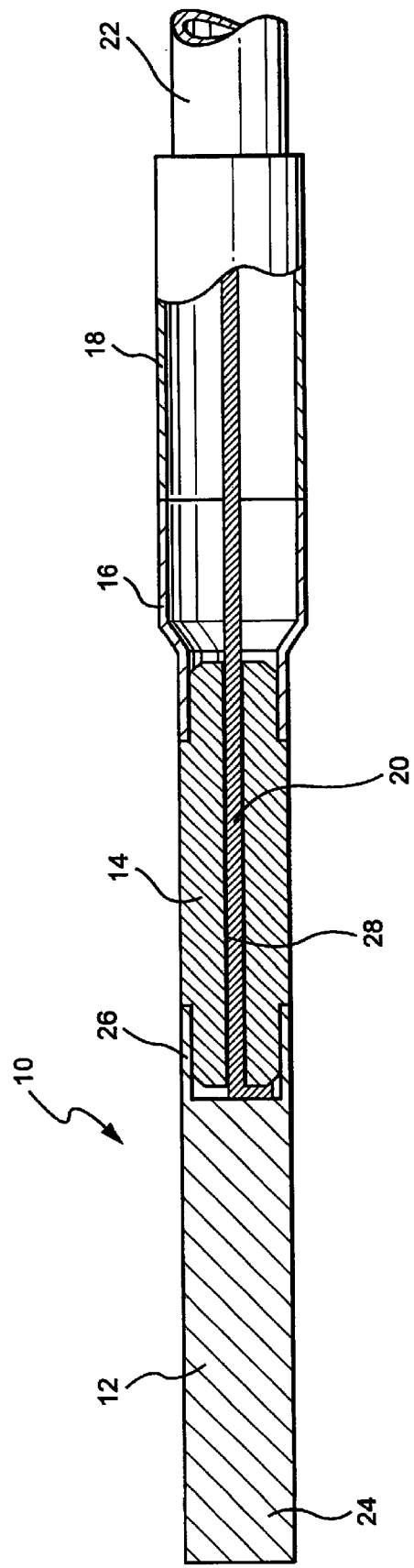
FIG. 1 is a partial cross-section of an ECP electrode in accordance with the exemplary embodiment of the invention.

Referring to FIG. 1, an ECP sensor electrode 10 generally includes an electrode tip 12, a cylindrical ceramic insulator 14, a metal adapter sleeve 16, a metal adapter housing 18, a steel center conductor wire 20 and a coaxial cable 22.

The zircalloy tip 12 of the electrode is closed at one end 24 with the other end 26 remaining open. The open end 26 of the zircalloy tip is brazed to one end of the cylindrical ceramic insulator 14 with a bore 28 in the center thereof. The ceramic insulator is preferably made from magnesia partially stabilized zirconia with a 3-mol % magnesia concentration. The zircalloy tip-to-ceramic insulator braze preferably utilizes a pure silver braze filler for the brazing process. The ceramic insulator 14 is brazed at its opposite end to the metal adapter sleeve 16 that is made from an iron-nickel alloy. The adapter sleeve-to-ceramic insulator braze preferably utilizes an active braze material consisting of a titanium-copper-silver braze alloy. The conductor wire 20 is attached to the inside of the open end of the zircalloy tip 12 by using a silver braze filler. The conductor wire 20 passes through the center of the zirconia ceramic insulator 14, and through the adapter sleeve 16 and adapter housing 18 and is electrically connected to the coaxial cable 22.

The iron-nickel alloy adapter sleeve 16 is welded to the stainless steel (or other equivalent alloy) adapter housing 18. The adapter housing 18 serves as a transition piece so that the electrode can be welded to the coaxial cable 22 that has a stainless steel outer sheath. The coaxial cable 22 is preferably mineral insulated with magnesia oxide or other suitable insulator surrounding the center wire 20. The coaxial cable 22 may be terminated in a suitable electrical connector (not shown) or may be sealed through the use of a suitable epoxy with the center wire 20 allowed to extend a small distance beyond the termination point of the coaxial cable.

As an alternate construction, the ceramic insulator 14 as well as a part of the zircalloy metal electrode tip 12 and the iron-nickel alloy adapter sleeve 16 may be coated with a magnesia partially-stabilized zirconia, or yttria partially-stabilized zirconia plasma spray to act as a thermal barrier and corrosion protectant.

Autoclave test data indicates that the zircalloy electrodes, when compared to a platinum reference electrode, responds to changes in hydrogen and oxygen concentrations as well as to changes in the temperature of the water. This will allow the zircalloy electrode to indicate the changes in the electrochemical corrosion potential of the zircalloy surface as water chemistry is adjusted and will also indicate the long-term change in the electrochemical corrosion potential of the zircalloy as it is exposed to a given environment.

The ECP electrode 10 may be used to measure the electrochemical corrosion potential of zircalloy metal in varying conditions of water chemistry in a coolant of, for example, a nuclear reactor, or other similar environment. These measurements will also aid the reactors in carrying out more efficient, more accurate, and more reliable monitoring for stress corrosion cracking and the overall corrosion taking place inside of the reactor and coolant loops.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. An electrochemical corrosion potential sensor electrode comprising an electrode tip having a closed end and an open end, said open end secured to a ceramic insulator, with a conductor wire extending through the insulator into the electrode tip, and wherein the electrode tip is constructed of zircalloy.

2. The electrochemical corrosion potential sensor electrode of claim 1 wherein said open end is brazed to one end of said ceramic insulator.

3. The electrochemical corrosion potential sensor electrode of claim 2 wherein said open end is brazed to said one end of said ceramic insulator utilizing a silver braze filler.

4. The electrochemical corrosion potential sensor electrode of claim 1 wherein an opposite end of said ceramic insulator is brazed to one end of a substantially cylindrical metal adapter sleeve.

5. The electrochemical corrosion potential sensor electrode of claim 4, wherein said opposite end of said ceramic insulator is brazed to said substantially cylindrical metal adapter sleeve utilizing a titanium-copper-silver braze alloy.

6. The electrochemical corrosion potential sensor electrode of claim 5 wherein said metal adapter sleeve is composed of an iron-nickel alloy.

7. The electrochemical corrosion potential sensor electrode of claim 6 wherein said ceramic insulator is composed of a magnesia partially-stabilized zirconia.

8. The electrochemical corrosion potential sensor electrode of claim 6 wherein said metal adapter sleeve is coated with a magnesia partially-stabilized zirconia or yttria partially-stabilized zirconia.

9. The electrochemical corrosion potential sensor electrode of claim 1 wherein said ceramic insulator is composed of a magnesia partially-stabilized zirconia.

10. The electrochemical corrosion potential sensor electrode of claim 1 wherein said ceramic insulator is coated with a magnesia partially-stabilized zirconia or yttria partially-stabilized zirconia.

11. The electrochemical corrosion potential sensor electrode of claim 1 wherein an opposite end of said metal adapter sleeve is secured to an adapter housing, wherein a coaxial cable is electrically connected to said conductor wire and secured to said adapter housing.

12. The electrochemical corrosion potential sensor electrode of claim 1 wherein said ceramic insulator is coated with a magnesia partially-stabilized zirconia or yttria partially-stabilized zirconia.

13. An electrochemical corrosion potential sensor electrode comprising a zircalloy electrode tip having a closed end and an open end, said open end secured to a ceramic insulator, and a conductor wire extending through the insulator into the electrode tip; wherein said open end is brazed to one end of said ceramic insulator; and an opposite end of said ceramic insulator is brazed to one end of a substantially cylindrical metal adapter sleeve; wherein an opposite end of said metal adapter sleeve is secured to an adapter housing, and further wherein a coaxial cable electrically connected to said conductor wire is secured to said adapter housing.

14. The electrochemical corrosion potential sensor electrode of claim 13 wherein said opposite end of said ceramic insulator is brazed to said substantially cylindrical metal adapter sleeve utilizing a titanium-copper-silver braze alloy.

15. The electrochemical corrosion potential sensor electrode of claim 13 wherein said metal adapter sleeve is composed of an iron-nickel alloy.

16. The electrochemical corrosion potential sensor electrode of claim 13 wherein said adapter housing and an outer sheath of said coaxial cable are composed of stainless steel.

\* \* \* \* \*